US011125687B2

(12) United States Patent
Zheng et al.

(10) Patent No.: US 11,125,687 B2
(45) Date of Patent: Sep. 21, 2021

(54) METHOD AND DEVICE FOR IDENTIFYING FRAGMENTED RED BLOOD CELLS, BLOOD CELL ANALYZER AND ANALYSIS METHOD

(71) Applicant: SHENZHEN MINDRAY BIO-MEDICAL ELECTRONICS CO., LTD., Shenzhen (CN)

(72) Inventors: Wenbo Zheng, Shenzhen (CN); Bo Ye, Shenzhen (CN); Huan Qi, Shenzhen (CN); Shan Yu, Shenzhen (CN); Xiujuan Li, Shenzhen (CN); Zhaoyang Li, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 16/537,674

(22) Filed: Aug. 12, 2019

(65) Prior Publication Data
US 2019/0360929 A1    Nov. 28, 2019

Related U.S. Application Data

(63) Continuation of application No. PCT/CN2017/073992, filed on Feb. 17, 2017.

(51) Int. Cl.
*G01N 21/00* (2006.01)
*G01N 21/49* (2006.01)
(Continued)

(52) U.S. Cl.
CPC ............. *G01N 21/49* (2013.01); *G01N 21/64* (2013.01); *G01N 33/49* (2013.01)

(58) Field of Classification Search
CPC ................... G01N 21/6486; G01N 21/6456
(Continued)

(56) References Cited

U.S. PATENT DOCUMENTS 5,264,369 A    11/1993  Sakata et al.
2001/0053551 A1  12/2001  Jiang et al.
(Continued)

FOREIGN PATENT DOCUMENTS

CN    101680879 A    3/2010
CN    103076311 A    5/2013
(Continued)

OTHER PUBLICATIONS

Extended European Search Report issued in the related European application 17896649.5, dated Aug. 21, 2020, 8 pages.

*Primary Examiner* — Natalia Levkovich
(74) *Attorney, Agent, or Firm* — Kory D. Christensen

(57) ABSTRACT

A method for identifying fragmented red blood cells comprising: acquiring side scatter light signals and fluorescence signals of cell particles in a sample liquid; and distinguishing and identifying a fragmented red blood cell population from the cell particles according to the side scatter light signals and the fluorescence signals of the cell particles. The fragmented red blood cell population can be identified from the cell particles by processing and analyzing the side scatter light signals and fluorescence signals of the sample liquid. The present application further provides a device for identifying fragmented red blood cells, a blood cell analyzer and an analysis method. Fragmented red blood cells can be identified according to the fluorescence that characterizes a nucleic acid content in a cell particle and the side scatter light, thus reducing errors in identification and counting.

9 Claims, 10 Drawing Sheets

(51) Int. Cl.
*G01N 21/64* (2006.01)
*G01N 33/49* (2006.01)

(58) Field of Classification Search
USPC .......................................... 422/82.05, 82.08
See application file for complete search history.

(56) References Cited

U.S. PATENT DOCUMENTS

| | | |
|---|---|---|
| 2010/0184061 A1 | 7/2010 | Kataoka et al. |
| 2012/0171659 A1* | 7/2012 | Guo ........................ G01N 35/00 435/3 |
| 2016/0018312 A1 | 1/2016 | Wu et al. |

FOREIGN PATENT DOCUMENTS

| | | |
|---|---|---|
| CN | 103364324 A | 10/2013 |
| CN | 103472034 A | 12/2013 |
| CN | 104297135 A | 1/2015 |
| CN | 104749144 A | 7/2015 |
| WO | WO 2018148946 A1 | 8/2018 |

* cited by examiner

| SAMPLE | MANUAL MICROSCOPIC INSPECTION RESULT OF FRAGMENTED RED BLOOD CELLS | RATIO OF PARTICLES IN THE SPECIFIC REGION OF FRAGMENTED RED BLOOD CELLS |
|---|---|---|
| Sample1 | 1.13% | 0.85% |
| Sample2 | 2.34% | 2.54% |
| Sample3 | 9.30% | 8.60% |
| Sample4 | 5.86% | 5.88% |

METHOD AND DEVICE FOR IDENTIFYING FRAGMENTED RED BLOOD CELLS, BLOOD CELL ANALYZER AND ANALYSIS METHOD

CROSS-REFERENCE TO RELATED APPLICATIONS

This application is a continuation of Patent Cooperation Treaty Application No. PCT/CN2017/073992, filed on Feb. 17, 2017, the content thereof is hereby incorporated by reference in its entirety.

TECHNICAL FIELD

The present application relates to the field of blood detection, and in particular to a method and a device for identifying fragmented red blood cells, a blood cell analyzer, and a blood cell analysis method.

BACKGROUND

In normal humans, the ratio of red blood cell fragments (schistocytes), i.e. fragmented red blood cells to all red blood cells is less than 1%. In a clinical setting, it is sometimes necessary to detect fragmented red blood cells in a blood sample for medical reference. Therefore, accurate and reliable counting of fragmented red blood cells is necessary.

In recent years, blood cell analyzers for counting and classifying blood cells by applying the principle of flow cytometry have been successively developed. Those analyzers are efficient and easy to operate, and have therefore significantly promoted the development of blood detection technologies.

SUMMARY

On such basis, it is necessary to provide a method and a device for identifying fragmented red blood cells, a blood cell analyzer, and a blood cell analysis method that have high precision in identifying fragmented red blood cells.

A method for identifying fragmented red blood cells is provided, comprising the following steps:
acquiring side scattered light signals and fluorescence signals of cell particles in a sample liquid; and
distinguishing and identifying a fragmented red blood cell population from the cell particles according to the side scattered light signals and the fluorescence signals of the cell particles.

A device for identifying fragmented red blood cells is provided, comprising:
an acquisition unit configured to acquire side scattered light signals and fluorescence signals of cell particles in a sample liquid; and
an identification unit configured to distinguish and identify a fragmented red blood cell population from the cell particles according to the side scattered light signals and the fluorescence signals of the cell particles.

In the above-mentioned method and the above-mentioned device for identifying fragmented red blood cells, a fragmented red blood cell population can be accurately identified from the cell particles by processing and analyzing side scattered light signals and fluorescence signals of the sample liquid. Fragmented red blood cells can be accurately identified and acquired based on fluorescence characterizing the nucleic acid content in the cell particles, and side scattered light. Fragmented red blood cell identification accuracy is thereby improved.

A blood cell analyzer is provided, comprising:
a sampling device configured to collect a blood sample;
a sample preparation device configured to treat the blood sample collected by the sampling device with a reagent to prepare a sample liquid;
a detection device configured to irradiate the sample liquid with light and collect optical information generated by cell particles in the sample liquid in response to the light irradiation, wherein the optical information includes side scattered light signals and fluorescence signals;
a conveying device configured to convey the sample liquid in the sample preparation device to the detection device and to make the cell particles in the sample liquid pass through a detection area of the detection device one by one; and
a processor configured to receive the optical information acquired by the detection device, and distinguish and identify a fragmented red blood cell population from the cell particles according to the optical information.

A blood cell analysis method is provided, comprising the following steps:
treating a blood sample to form a sample liquid;
acquiring optical information of cell particles in the sample liquid, wherein the optical information includes side scattered light signals and fluorescence signals; and
distinguishing and identifying a fragmented red blood cell population from the cell particles according to the optical information.

In the aforesaid blood cell analyzer and the aforesaid blood cell analysis method, a fragmented red blood cell population can be distinguished and identified from the cell particles according to side scattered light signals and fluorescence signals of the cell particles. The acquired fragmented red blood cell count accuracy is higher than that in the prior art, thereby reducing errors in identifying and counting of the fragmented red blood cell population.

Details of one or more embodiments of the present application are set forth in the accompanying drawings and description below. Other features, objectives, and advantages of the present application will become apparent from the description, accompanying drawings, and claims.

DETAILED DESCRIPTION OF THE EMBODIMENTS

In order to facilitate the understanding of the present application, the present application will be described in detail hereinafter with reference to the accompanying drawings. Preferred embodiments of the present application are provided in the accompanying drawings. However, the present application may be embodied in many different forms and is not limited to the embodiments described herein. Rather, these embodiments are provided for a more thorough understanding of the present disclosure.

In the prior art, an identification method for counting fragmented red blood cells is provided, comprising:

(1) staining blood cells with a nucleic acid dye; allowing the blood cells flow through a detection area one by one; measuring forward scattered light information and fluorescence information for each cell; dividing, according to the scatter light information and the fluorescence information, the cells into three categories: white blood cells, red blood cells, and platelets; wherein a number of particles in the red blood cell region is denoted as A;

(2) identifying fragmented red blood cells falling within a preset region on a two-dimensional scattergram prepared from the fluorescence and the forward scattered light, wherein a number of particles falling within the fragmented red blood cell region is denoted as B;

(3) establishing a small red blood cell region on the two-dimensional scattergram prepared from the fluorescence and the forward scattered light, wherein a number of particles falling within the small red blood cell region is denoted as C; and (4) acquiring a final counting number of the fragmented red blood cells, and denoting the ratio of the number of the fragmented red blood cells to the number of the red blood cells as FRC %, which ratio is calculated according to the following method:

$$FRC \% = \frac{B}{A} \quad \text{when} \quad \frac{C}{A} \leq = \alpha$$

$$FRC \% = \frac{B}{A} \times \text{EXP}\left(-\alpha \times \frac{C}{A}\right) \quad \text{when} \quad \frac{C}{A} > \alpha$$

Wherein α is a constant in a range of 1% to 3%.

However, it has been found through study that, when the small red blood cells overlap heavily with the fragmented red blood cells, a large error exists between the FRC % acquired by the above method and that acquired by manual microscopic inspection.

Figure 1:
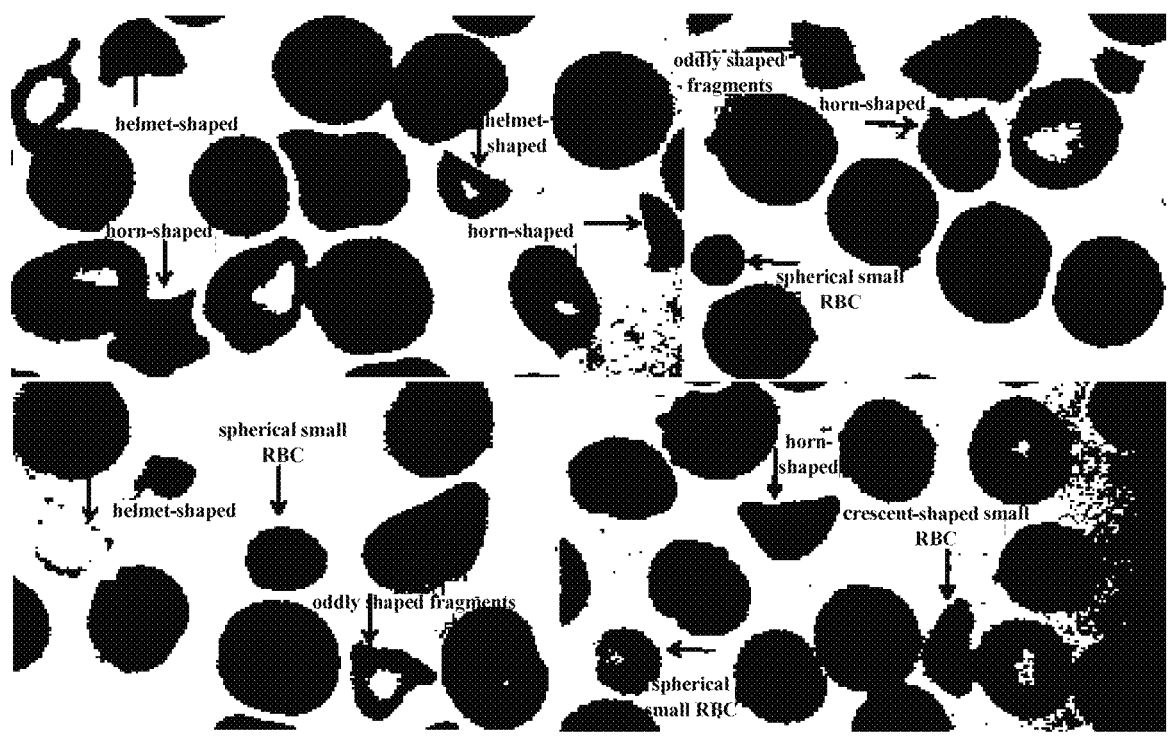
FIG. 1 illustrates a blood cell image of a blood sample under a microscope provided in the prior art.
Figure 2:
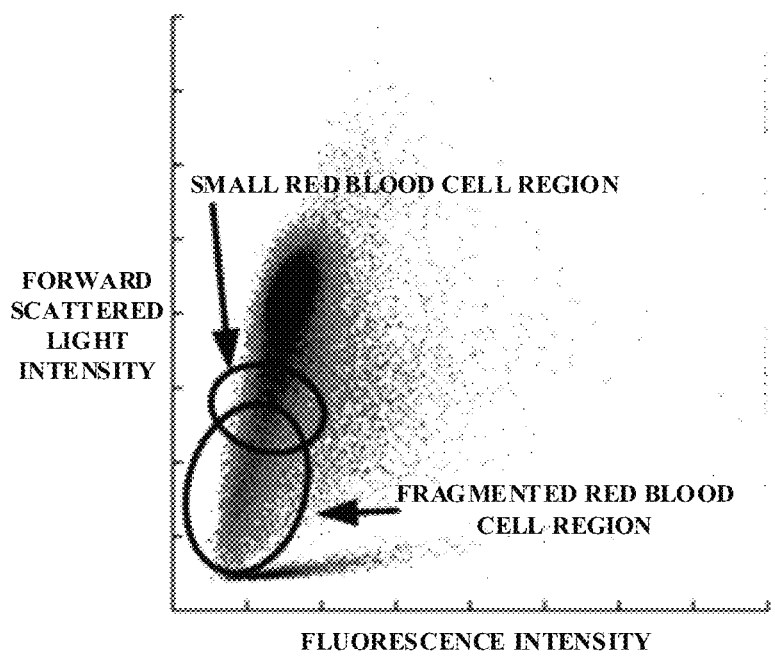
FIG. 2 illustrates a two-dimensional scattergram prepared from forward scattered light signals and fluorescence signals of the blood sample shown in FIG. 1.

The inventors of the present application discovered the following through research on current methods for identifying fragmented red blood cells. As shown in FIGS. 1 and 2, forward scattered light signals and fluorescence signals are used for identification, wherein forward scattered light characterizes a cell volume. When a relatively high quantity of small red blood cells exists in a sample due to a certain disease, the smaller volume of small red blood cells makes it easy for them to be mixed up with fragmented red blood cells, thus influencing the counting of fragmented red blood cells. FIG. 1 shows a schematic diagram of blood cells under a microscope during microscopic inspection, and FIG. 2 shows a two-dimensional scattergram of forward scattered light signals and fluorescence signals for identifying fragmented red blood cells. As shown in FIG. 1, the fragmented red blood cells are respectively helmet-shaped or horn-shaped, the small red blood cells are respectively spherical or crescent-shaped, and the small red blood cells are easily mixed up with the fragmented red blood cells, resulting in low accuracy of identification and counting. As shown in FIG. 2, the region of the fragmented red blood cells in the blood sample is adjacent to that of the small red blood cells, and both are partially overlapped. The count value of the fragmented red blood cells acquired from FIG. 2 is 14.5%, and the count value of the fragmented red blood cells acquired from microscopic inspection is 7.2%.

Therefore, a novel method is required for improving identification accuracy of fragmented red blood cells, so as to improve counting accuracy of the fragmented red blood cells.

Figure 3:
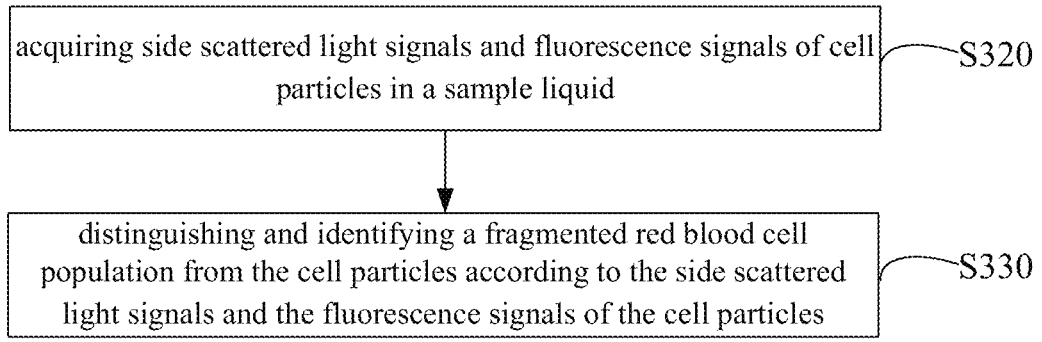
FIG. 3 illustrates a flowchart of a method for identifying fragmented red blood cells according to an embodiment of the present application.

As shown in FIG. 3, an embodiment of the present application provides a method for identifying fragmented red blood cells, which comprises the following steps:

S320: acquiring side scattered light signals and fluorescence signals of cell particles in a sample liquid.

A sample liquid refers to a sample acquired after reaction of a blood sample with a reagent. In one implementation, optical information of cell particles in the sample liquid is acquired by a blood cell analyzer. Specifically, a conveying device is automatically controlled to convey the sample liquid to a detection device of the blood cell analyzer and make the cell particles in the sample liquid pass through a detection area of the detection device one by one, and then side scattered light signals and fluorescence signals of the cell particles in the sample liquid are collected. The automatically controlled conveying of the sample liquid by the conveying device reduces human influence and improves identification accuracy.

In this embodiment, the detected and collected optical information of the cell particles includes side scattered light signals and fluorescence signals for identifying fragmented red blood cells. During specific implementations, the optical information may also include other information required for detection, which is not limited herein.

S330: distinguishing and identifying a fragmented red blood cell population from the cell particles according to the side scattered light signals and the fluorescence signals of the cell particles.

While not wishing to be bound by theory, the applicant found in researches that, due to the damage of cell membranes of the fragmented red blood cells, non-specific binding of proteins on the cell membranes of the fragmented red blood cells to a dye in the reagent is reduced, and the fluorescent signals are weakened. Therefore, the fragmented red blood cells would generate relatively weak fluorescence signals. Meanwhile, due to the loss of intracellular hemoglobin in the fragmented red blood cells, the side scattered light signals thereof that characterize cellular content are weakened. Therefore, the fragmented red blood cells would generate weak side scattered light signals. After repeated researches and verifications, it is found that by processing and analyzing the side scattered light signals and the fluorescence signals of the sample liquid, a fragmented red blood cell population can be accurately identified from the cell particles, and the fragmented red blood cells can further be identified. By means of the method for identifying fragmented red blood cells in this embodiment, the fragmented red blood cells can be accurately identified according to the fluorescence that characterizes the nucleic acid content in the cell particles, and the side scattered light, thus reducing errors in identification and counting of fragmented red blood cells.

Figure 4:
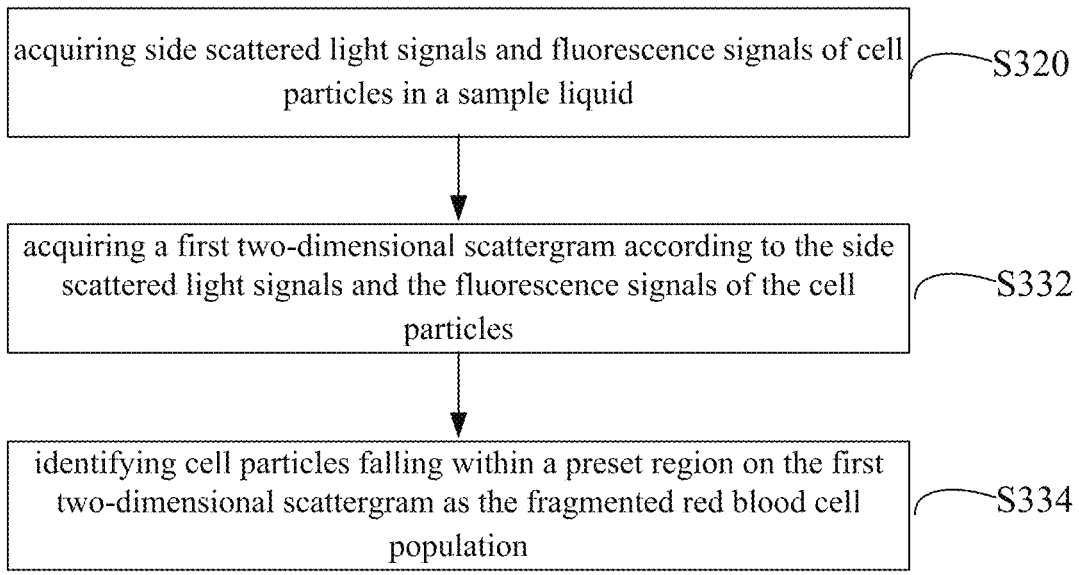
FIG. 4 illustrates a flowchart of a method for identifying fragmented red blood cells according to another embodiment of the present application.

In one embodiment, as shown in FIG. 4, step S330 comprises:

S332: acquiring a first two-dimensional scattergram according to the side scattered light signals and the fluorescence signals of the cell particles.

In one implementation, the detected and collected side scattered light signals and fluorescence signals of the cell particles are converted into corresponding electrical signals. Specifically, the side scattered light signals and the fluorescence signals, which are generated by the cell particles to be tested in response to the light irradiation, are converted into corresponding electrical signals by a photoelectric sensor, and then the electrical signals are converted into corresponding digital signals by an A/D converter, so as to acquire a side scattered light intensity and a fluorescence intensity of each cell particle as well as to establish a corresponding relation between the side scattered light intensity and the fluorescence intensity of each cell particle. A first two-dimensional scattergram is thus acquired.

S334: identifying cell particles falling within a preset region on the first two-dimensional scattergram as the fragmented red blood cell population.

The preset region may be a specific region on the first two-dimensional scattergram, which specific region is acquired by comparing two-dimensional scattergrams of normal human blood samples and blood samples containing fragmented red blood cells and then conducting statistical analysis. According to parameters of the specific region, on the first two-dimensional scattergram of an unknown blood sample, a cell population falling within the preset region is identified as the fragmented red blood cell population.

In another implementation, it is also possible to compare normal human blood samples with blood samples containing fragmented red blood cells and then conduct statistical analysis, so as to acquire a function of the relative position between a fragmented red blood cell population region and a normal human red blood cell population region or other normal human cell population regions. Using the aforementioned function, the preset region of an unknown blood sample is determined according to an identified red blood cell population region on the first two-dimensional scattergram of the unknown blood sample.

On the scattergram where the X-axis represents the fluorescence intensity and the Y-axis represents the side scattered light intensity, the overall fluorescence intensity of the fragmented red blood cell population is lower than that of the red blood cell population, and the overall side scattered light intensity of the fragmented red blood cell population is also lower than that of the red blood cell population. That is, the preset region is located at the lower left of the red blood cell population. It should be noted that, the fact that the overall fluorescence intensity of the fragmented red blood cell population is lower than that of the red blood cell population and the overall side scattered light intensity of the fragmented red blood cells population is also lower than that of the red blood cell population, does not mean that the fluorescence intensity and side scattered light intensity of every cell particle in the fragmented red blood cell population are lower than the fluorescence intensity and side scattered light intensity of cell particles in the red blood cell population.

The number of particles falling within the preset region on the two-dimensional scattergram acquired by the side scattered light signals and the fluorescence signals has a strong correlation with the existing of fragmented red blood cells.

Cell membranes of the fragmented red blood cells are damaged, thus the specific binding of proteins on the cell membranes to a reagent would be reduced, and the fluorescence signals would thus be weakened. Therefore, the fragmented red blood cells would generate relatively weak fluorescence signals. Meanwhile, the fragmented red blood cells are mechanically damaged inside, resulting in the loss of the intracellular hemoglobin, and the side scattered light signals that characterize cell content would thus be weakened. Therefore, the fragmented red blood cells would generate weak side scattered light signals. By processing and analyzing the side scattered light signals and the fluorescence signals of the sample liquid, on the two-dimensional scattergram acquired from the side scattered light signals and the fluorescence signals, a cell population falling within the preset region is determined as the fragmented red blood cell population.

Figure 5:
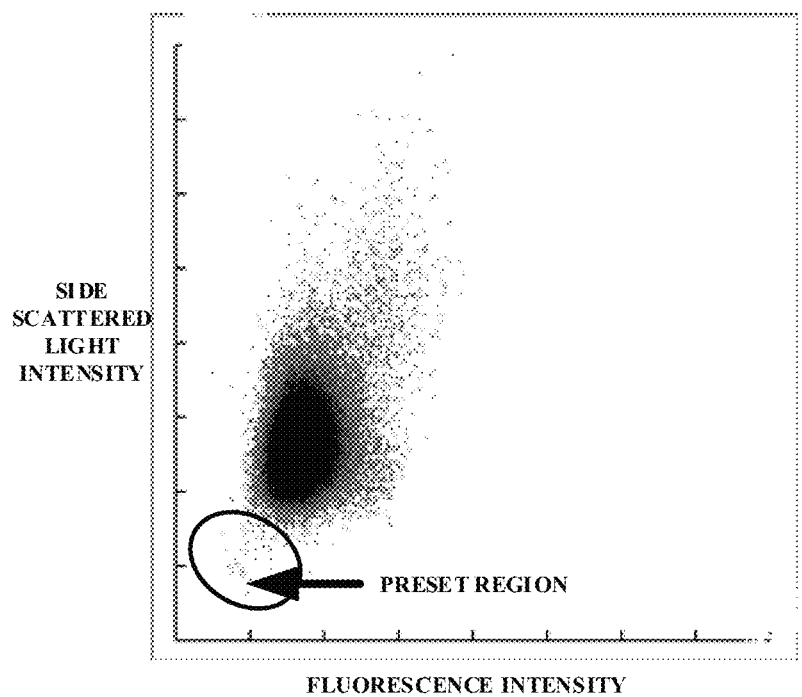
FIG. 5 illustrates a two-dimensional scattergram prepared from side scattered light signals and fluorescence signals of a normal blood sample provided in the present application.
Figure 6:
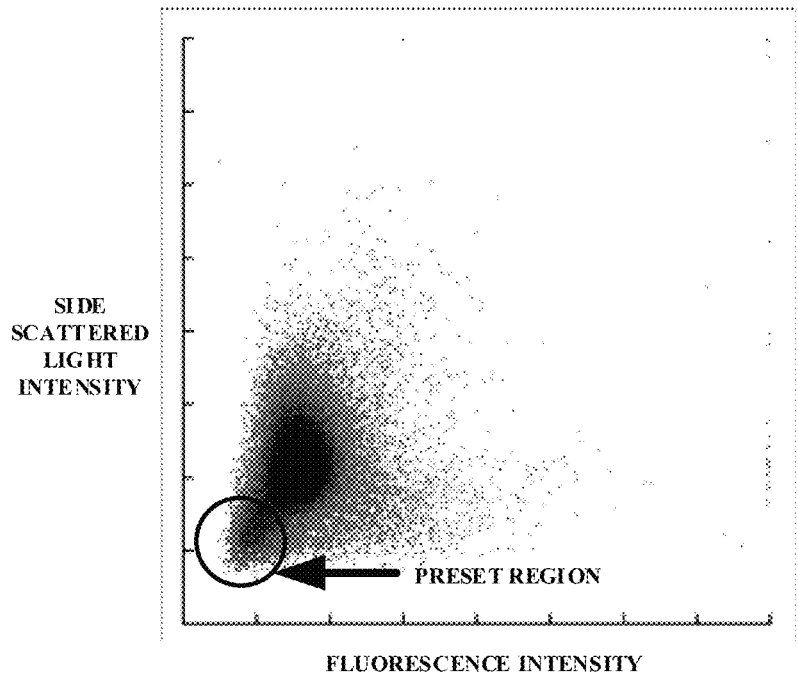
FIG. 6 illustrates a two-dimensional scattergram prepared from side scattered light signals and fluorescence signals of a blood sample containing fragmented red blood cells provided in the present application.

For ease of explanation, please refer to FIGS. 5 and 6, where a two-dimensional scattergram of side scattered light signals and fluorescence signals of a normal sample liquid (see FIG. 5) and a two-dimensional scattergram of side scattered light signals and fluorescence signals of a sample liquid containing fragmented red blood cells (see FIG. 6) are provided, wherein, the abscissa represents the fluorescence intensity of cell particles, and the ordinate represents the side scattered light intensity of cell particles. As can be seen from FIGS. 5 and 6, cell particles falling within the preset region are fragmented red blood cells. Each cell particle in the sample liquid is reflected on the first two-dimensional scattergram according to its fluorescence intensity and side scattered light intensity, so as to distinguish different cell populations.

Thus, fragmented red blood cells can be identified according to a characteristic region on a scattergram prepared from fluorescence and side scattered light, and the accuracy of the acquired count value of fragmented red blood cells is higher than that in the prior art.

It should be understood that in the present application, a cell population having an overall fluorescence intensity lower than that of the red blood cell population and an overall side scattered light intensity lower than that of the red blood cell population is identified as the fragmented red blood cell population. Specifically, in the above-described implementation, on the first two-dimensional scattergram, cell particles located in the lower left region of the red blood cell population are identified as the fragmented red blood cell population. However, in some other implementations, it is not limited to the two-dimensional scattergram, which is not limited herein.

In one embodiment, after step S330, the method further comprises the following step:

counting cell particles in the fragmented red blood cell population.

Specifically, the counting of the fragmented red blood cells may be acquired by using a known statistical method for cell particles in the prior art, and the specific statistical principle thereof is not further described herein.

In one embodiment, the method for identifying fragmented red blood cells further comprises the following step:

displaying the fragmented red blood cell population.

In one implementation, the fragmented red blood cell population is displayed by distinctively displaying the fragmented red blood cells and other blood cells in a visual way, and specifically, with a color or a shape, or by drawing a boundary or an outline, etc. For example, in the foregoing first two-dimensional scattergram or other two-dimensional or three-dimensional scattergrams, the red blood cells and the fragmented red blood cells can be visually and distinctively displayed on the first two-dimensional scattergram according to information that characterizes the fragmented red blood cells, such as displayed as scattered points with different colors/shapes, or different particle populations are distinguished by drawing respective boundaries or outlines.

In one embodiment, the method for identifying fragmented red blood cell further comprises:

acquiring a count value of the fragmented red blood cell population according to the fragmented red blood cell population identified in step S330;

acquiring a count value of a red blood cell population in the sample liquid, for example, acquiring the count value of the red blood cell population of the sample liquid by means of other measurement methods, such as an impedance method; and acquiring a count ratio according to the count value of the fragmented red blood cell population and the count value of the red blood cell population.

Figure 7:
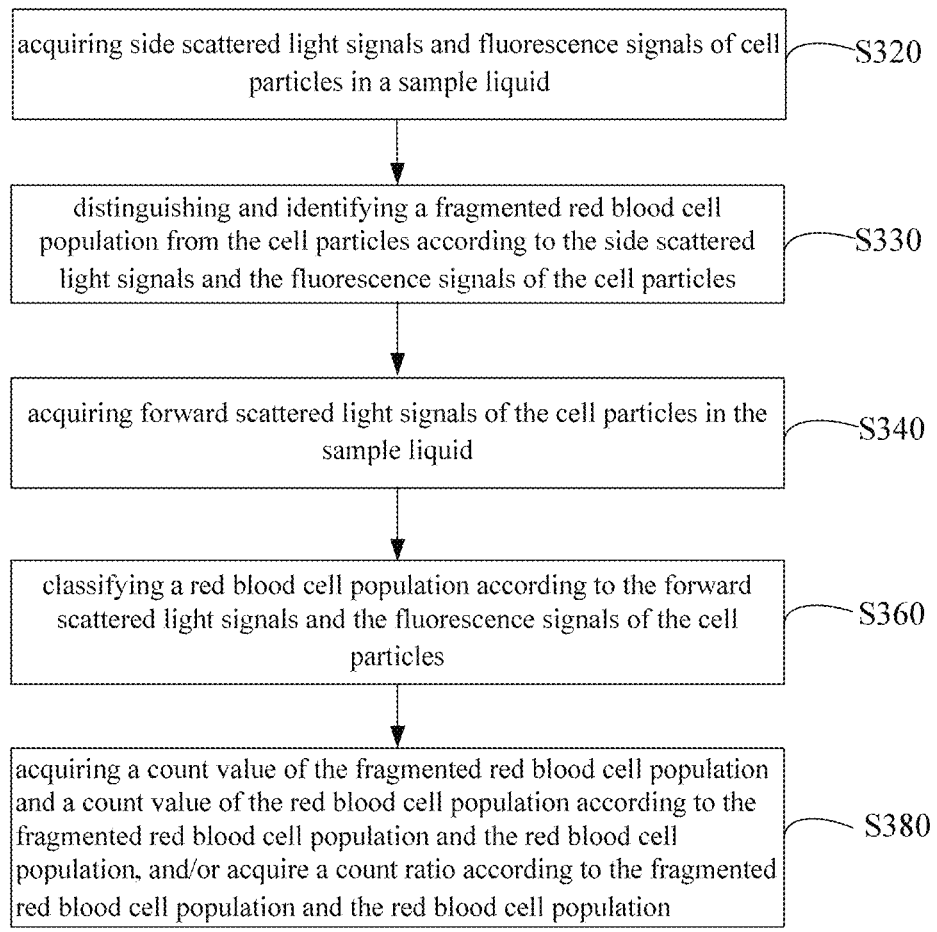
FIG. 7 illustrates a flowchart of a method for identifying fragmented red blood cells according to yet another embodiment of the present application.

In another embodiment, with reference to FIG. 7, the method for identifying fragmented red blood cells further comprises:

S340: acquiring forward scattered light signals of the cell particles in the sample liquid.

In one implementation, a flow blood cell analyzer can be used to irradiate the sample liquid with light, detect and collect optical information of the cell particles in the blood one by one, and simultaneously acquire forward scattered light signals, side scattered light signals, and fluorescence signals of the cell particles in the sample liquid.

S360: classifying a red blood cell population according to the forward scattered light signals and the fluorescence signals of the cell particles.

S380: acquiring a count value of the fragmented red blood cell population and a count value of the red blood cell population according to the fragmented red blood cell population and the red blood cell population, and/or acquire a count ratio according to the fragmented red blood cell population and the red blood cell population.

The count values of the above two cell populations may be acquired according to the fragmented red blood cell population and the red blood cell population, or the count ratio of the both may be acquired directly according to the fragmented red blood cell population and the red blood cell population without acquiring the count values of the above two kinds of cell populations. Certainly, the count values of the above two kinds of particle populations and the count ratio may be acquired according to the fragmented blood cell population and the red blood cell population.

Since the forward scattered light usually characterizes a cell volume, cell particles can be classified using the forward scattered light signals and the fluorescence signals, so as to distinguish and identify a red blood cell population. Since the side scattered light signal usually characterizes a cell content, fragmented red blood cells that lose intracellular hemoglobin can be identified using the side-scattered light signals and the fluorescence signals, so as to identify and distinguish a fragmented red blood cell population. By accurately identifying and distinguishing the red blood cell population and the fragmented red blood cell population, the count values and/or the count ratio of the fragmented red blood cell population and the red blood cell population can be acquired, so as to acquire accurate and reliable diagnostic information related to the fragmented red blood cells.

It should be understood that step S340 and step S320 can be performed simultaneously. The sequence of step S330 of distinguishing and identifying a fragmented red blood cell population from the cell particles according to the side scattered light signals and the fluorescence signals of the cell particles and step S360 of classifying the cell particles in the sample liquid according to the forward scattered light signals and the fluorescence signals of the cell particles for distinguishing and identifying a red blood cell population, is not limited. For example, in another embodiment, it is also possible to classify the red blood cell population first, and then identify the fragmented red blood cell population from the cell particles.

In one embodiment, before step S380, the method further comprises:

counting cell particles in the red blood cell population and cell particles in the fragmented red blood cell population.

The count ratio of the fragmented red blood cell population to the red blood cell population generally refers to the proportion of the fragmented red blood cell quantity in relation to the red blood cell quantity. A counting method of the red blood cells and a statistical method of the fragmented red blood cells may be both available from known statistical methods for cell particles in the prior art, and the specific statistical principles thereof are not described herein. The count value of the identified fragmented red blood cells is denoted as Frag_num, and the count value of the identified red blood cells is denoted as Rbc_Total, and the percentage of the fragmented red blood cells (that is, the count ratio of the fragmented red blood cell population to the red blood cell population) is denoted as FRC %, which is calculated according to the following formula:

$$FRC\ \% = \frac{Frag\_num}{Rbc\_Total} \times 100\%$$

By using this formula, the percentage of the fragmented red blood cell population to the red blood cell population can be calculated. The calculation result acquired by the counting method for fragmented red blood cells of the present application is substantially consistent with the ratio of fragmented red blood cells acquired manually under a microscope.

In one embodiment, step S360 comprises:

acquiring a second two-dimensional scattergram according to the forward scattered light signals and the fluorescence signals of the cell particles; and classifying the red blood cell population from the cell particles according to the second two-dimensional scattergram.

Figure 8:
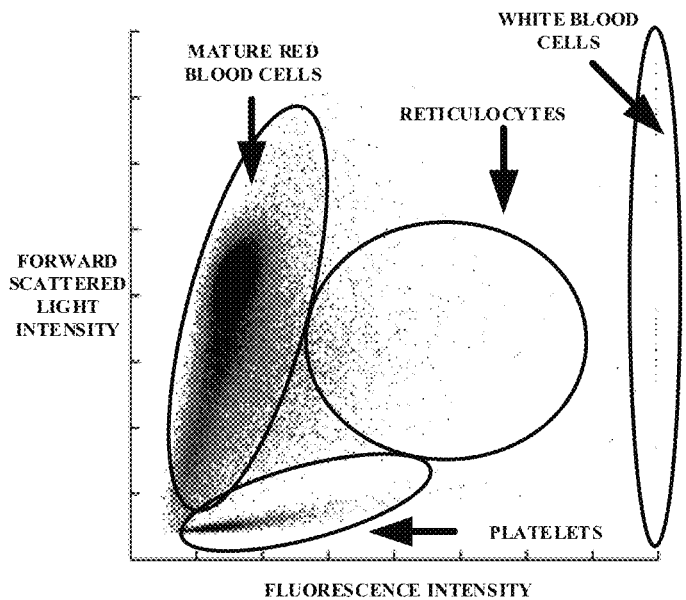
FIG. 8 illustrates a two-dimensional scattergram prepared from forward scattered light signals and fluorescence signals of a blood sample containing fragmented red blood cells provided in the present application.

In one implementation, at least one kind of reticulocytes, platelets, and white blood cells are classified and/or counted according to the second two-dimensional scattergram. By identifying and classifying the red blood cell population, the reticulocyte population, the white blood cell population, and the platelet population, the red blood cell population can be counted. With reference to FIG. 8, each cell particle in the sample liquid will be reflected on the second two-dimensional scattergram according to its fluorescence intensity and forward scattered light intensity. In FIG. 8, mature red blood cells are located in the middle of the left side of the second two-dimensional scattergram, forming the mature red blood cell population; platelets are located in the lower region of the second two-dimensional scattergram, forming the platelet population; white blood cells are located in the right side region of the second two-dimensional scattergram, forming the white blood cell population. The identification and classification of the white blood cell population, the red blood cell population, and the platelet population from the cell particles can be implemented by means of blood cell classification and identification technologies in the prior art, and the specific implementation principles thereof are not described herein.

Figure 9:
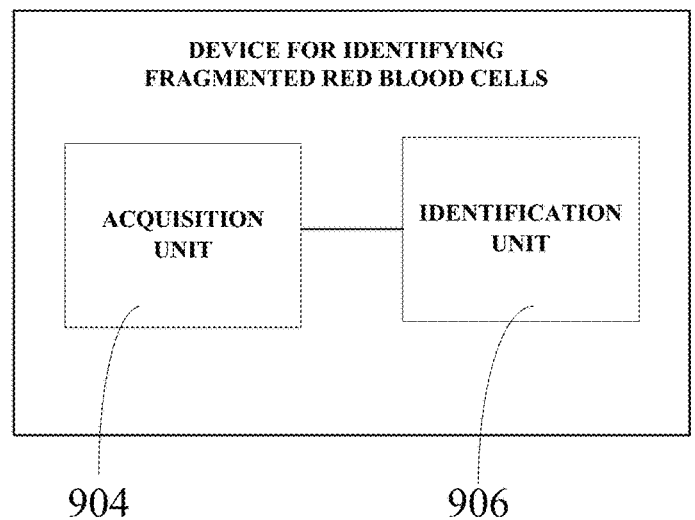
FIG. 9 illustrates a schematic structural diagram of a device for identifying fragmented red blood cells according to an embodiment of the present application.

As shown in FIG. 9, another embodiment of the present application further provides a device for identifying fragmented red blood cells, comprising:

an acquisition unit 904 configured to acquire side scattered light signals and fluorescence signals of cell particles in a sample liquid; and an identification unit 906 configured to distinguish and identify a fragmented red blood cell population from the cell particles according to the side scattered light signals and the fluorescence signals of the cell particles.

The device for identifying fragmented red blood cells in this embodiment identifies and acquires fragmented red blood cells through analyzing the fluorescence and the side scattered light. The accuracy of identifying and counting fragmented red blood cells in such way is higher than that in the prior art.

Figure 10:
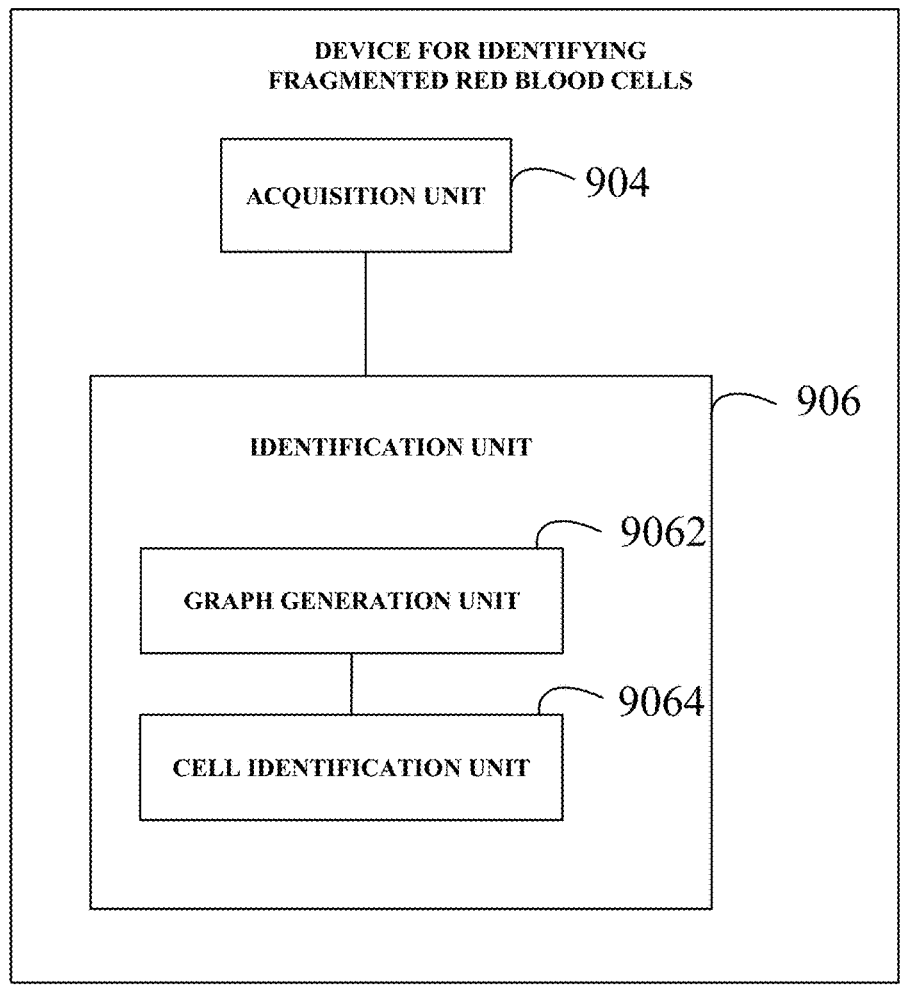
FIG. 10 illustrates a schematic structural diagram of a device for identifying fragmented red blood cells according to another embodiment of the present application.

In one embodiment, as shown in FIG. 10, the identification unit 906 comprises:

a graph generation unit 9062 configured to acquire a first two-dimensional scattergram according to the side scattered light signals and the fluorescence signals of the cell particles; and a cell identification unit 9064 configured to identify cell particles falling within a preset region on the first two-dimensional scattergram as the fragmented red blood cells.

In one implementation, the identification unit is specifically configured to identify a cell population having an overall fluorescence intensity lower than that of a red blood cell population and an overall side scattered light intensity lower than that of the red blood cell population as the fragmented red blood cell population. On the scattergram where the X-axis represents the fluorescence intensity and the Y-axis represents the side scattered light intensity, the overall fluorescence intensity of the fragmented red blood cell population is lower than that of the red blood cell population, and the overall side scattered light intensity of the fragmented red blood cell population is also lower than that of the red blood cell population. That is, the preset region is located at the lower left of the red blood cell population.

It should be understood that in this embodiment, the cell identification unit identifies, according to the first two-dimensional scattergram, a cell population having an overall fluorescence intensity lower than the fluorescence intensity of the red blood cell population and an overall side scattered light intensity also lower than that of the red blood cell population as the fragmented red blood cell population. In some other embodiments, it may not be limited to a scattergram, for example, the fluorescence intensity and the side-scattered light intensity of each cell can be analyzed only in a data form without generating a scattergram.

In the device for identifying fragmented red blood cells provided in this embodiment, the cell identification unit 9064 can accurately identify and acquire the fragmented red blood cell population according to the fluorescence signals characterizing the nucleic acid content in the cell particles and the side scattered light signals characterizing the cell content, and can accurately calculate a count ratio related to the fragmented red blood cell population by accurately identifying the fragmented red blood cell population, thus reducing errors in identifying fragmented red blood cells.

In one embodiment, the acquisition unit 904 is further configured to acquire forward scattered light signals of the cell particles in the sample liquid; and the identification unit 906 is further configured to classify the cell particles in the sample liquid according to the forward scattered light signals and the fluorescence signals of the cell particles, for distinguishing and identifying the red blood cell population.

Figure 11:
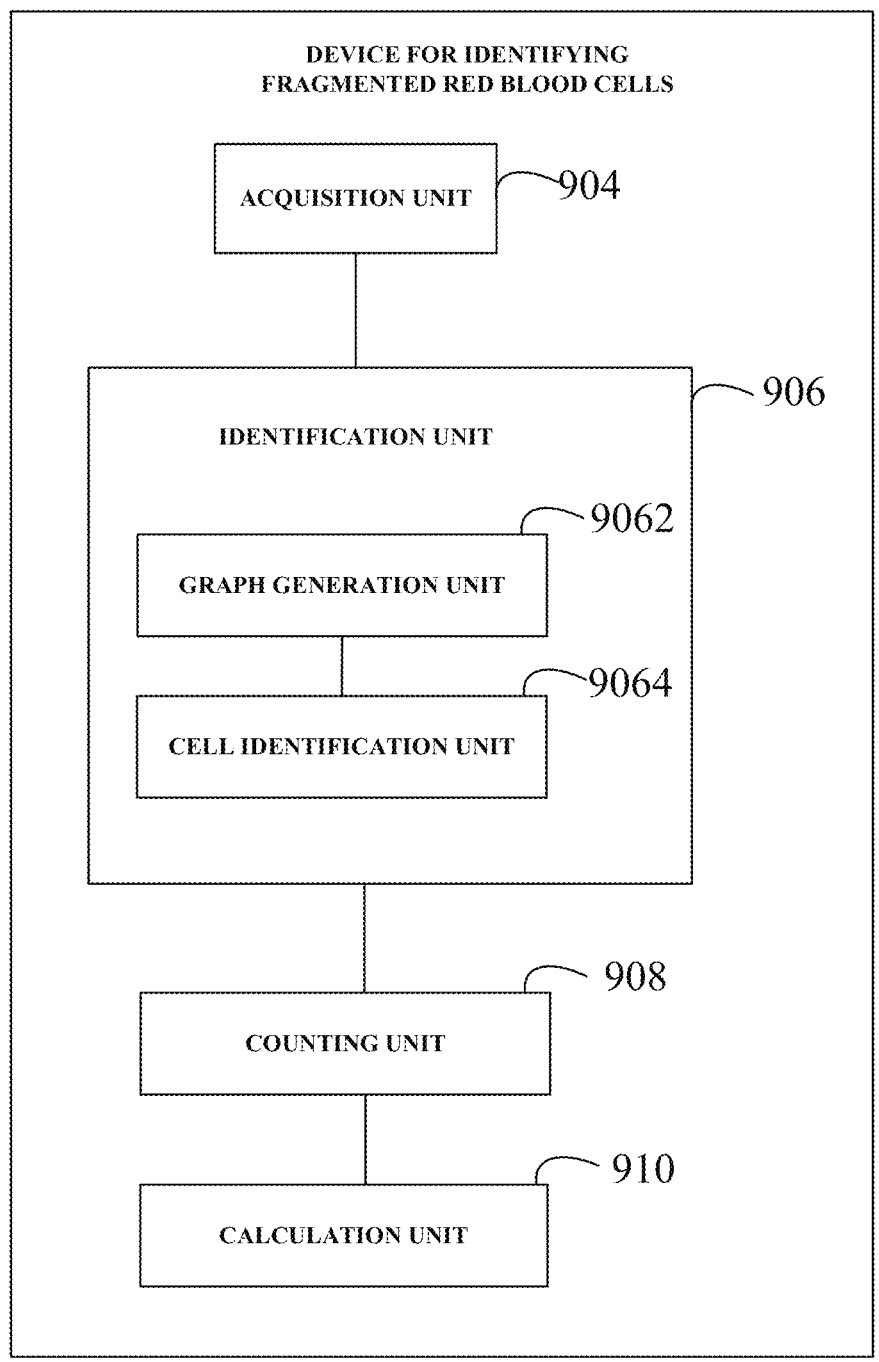
FIG. 11 illustrates a schematic structural diagram of a device for identifying fragmented red blood cells according to yet another embodiment of the present application.

In one embodiment, with reference to FIG. 11, the device for identifying fragmented red blood cells further comprises:

a counting unit 908 configured to count cell particles in the red blood cell population, and/or count cell particles in the fragmented red blood cell population.

In one embodiment, the device for identifying fragmented red blood cells further comprises:

a calculation unit 910 configured to acquire a count ratio according to the count value of the fragmented red blood cell population and the count value of the red blood cell population, or configured to acquire a count ratio according to the fragmented red blood cell population and the red blood cell population.

It should be understood that the calculation unit may acquire the count ratio according to the fragmented red blood cell population and the red blood cell population. For example, the corresponding count values can be acquired by respectively counting the fragmented red blood cell population and the red blood cell population using the counting unit, and then the count ratio can be calculated. The count value of the fragmented red blood cells may be acquired by counting the fragmented red blood cell population identified according to the forward scattered light signals and the fluorescence signals of the cell particles. The count value of the red blood cell population of the sample liquid may also be acquired by using other measurement methods such as an impedance method, which is not limited herein. Certainly, the calculation unit may also directly acquire the count ratio according to the fragmented red blood cell population and the red blood cell population, and it is not limited to acquiring the count ratio after acquiring the count values of the two kinds of cell populations.

The device for counting fragmented red blood cells provided in the present application distinguishes and identifies the fragmented red blood cell population from the cell particles according to the side scattered light signals and the fluorescence signals of the cell particles. The accuracy of the acquired count value of fragmented red blood cells is higher than that in the prior art, thereby reducing errors in counting and identifying fragmented red blood cell population.

In one embodiment, the graph generation unit 9062 is further configured to acquire a second two-dimensional scattergram according to the forward scattered light signals and the fluorescence signals of the cell particles.

The cell identification unit 9064 is further configured to classify the red blood cell population according to the second two-dimensional scattergram.

Specifically, at least one kind of reticulocytes, platelets, and white blood cells are classified and/or counted according to the second two-dimensional scattergram. By identifying and classifying the red blood cell population, the reticulocyte population, the white blood cell population and the platelet population, the red blood cell population can be counted.

Figures 12, 13:
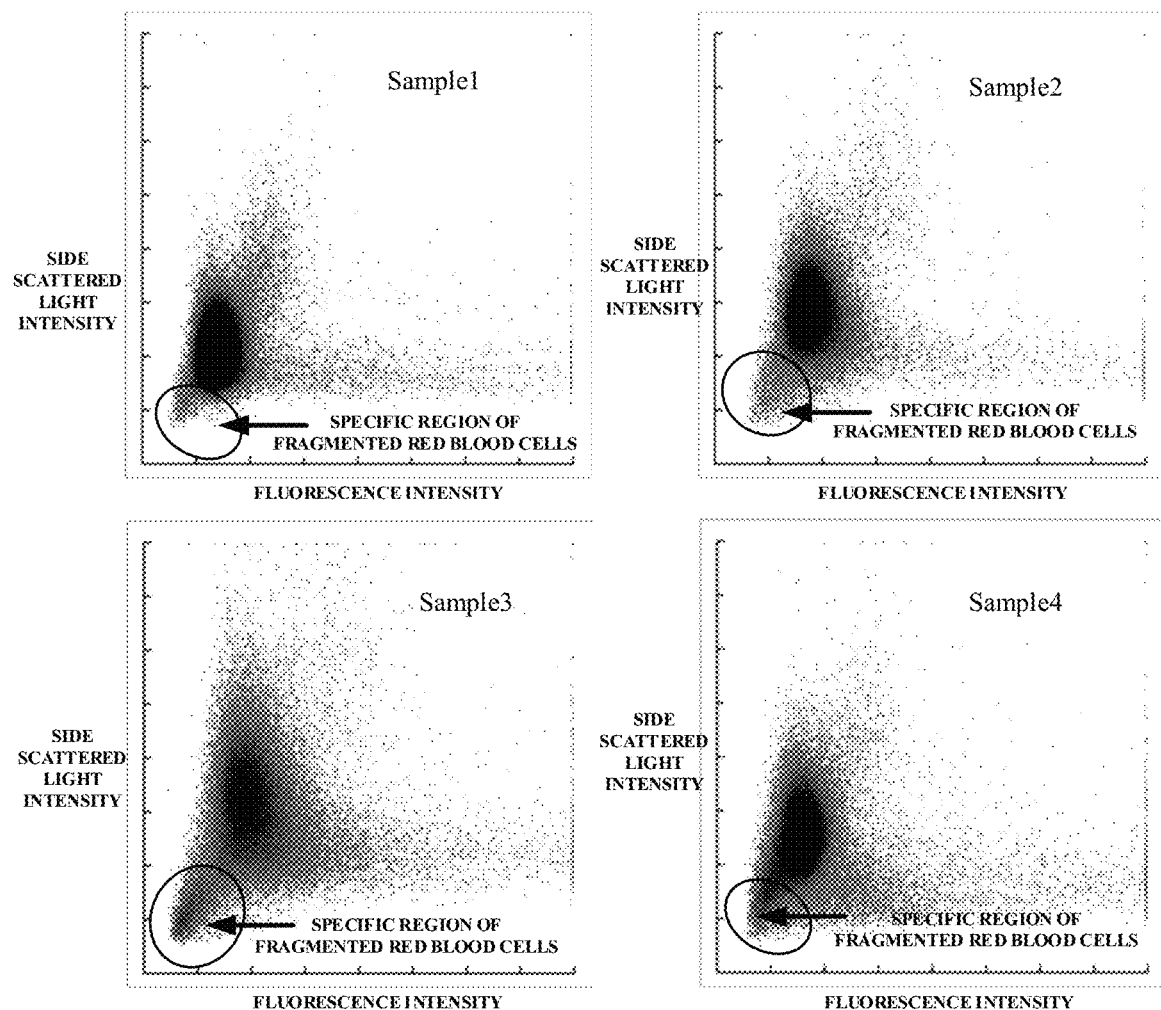
FIG. 12 illustrates two-dimensional scattergrams prepared from side scattered light signals and fluorescence signals of four blood samples provided in the present application.
FIG. 13 illustrates a comparison result diagram of fragmented red blood cell count values acquired from two-dimensional scattergrams of side scattered light signals and fluorescence signals, and manual count values of fragmented red blood cells for the four blood samples provided in the present application.

With reference to FIGS. 12 and 13, FIG. 12 shows first two-dimensional scattergrams of four blood samples selected from first two-dimensional scattergrams acquired by the graphic generation unit 9062 of the device for identifying fragmented red blood cells provided in an embodiment of the present application; FIG. 13 shows a comparison result diagram of fragmented red blood cell ratios and red blood cell manual microscopic inspection ratios of the four selected blood samples. It can be seen from FIGS. 12 and 13 that, the count ratios of fragmented red blood cell identified in the preset region of the first two-dimensional scattergrams of the four blood samples to red blood cells of the four blood samples are substantially consistent with the results of the four blood samples acquired by manual microscopic inspection, which proves by practice that adverse effects caused by identification and counting errors on the diagnosis and treatment of diseases are reduced.

Preferably, the device for counting fragmented red blood cells may be a processor of a red blood cell analyzer. During specific implementations, the device for counting fragmented red blood cells may also be other detection devices for detecting a count ratio of a fragmented red blood cell quantity and a red blood cell quantity.

In one embodiment, the acquisition unit is further configured to acquire forward scattered light signals of the cell particles in the sample liquid, and the identification unit is further configured to classify at least one kind of reticulocytes, platelets, and white blood cells according to the forward scattered light signals and the fluorescence signals.

In one embodiment, the device for identifying fragmented red blood cells further comprises a display unit, and the display unit is configured to display the fragmented red blood cell population.

Specifically, the fragmented red blood cell population is displayed by distinctively displaying the fragmented red blood cells and other blood cells in a visual way, for example, with a color or a shape, or by drawing a boundary or an outline, etc. More specifically, in the foregoing first two-dimensional scattergram or other two-dimensional or three-dimensional scattergrams, the red blood cells and the fragmented red blood cells can be visually and distinctively displayed on the first two-dimensional scattergram according to information characterizing the fragmented red blood cells, such as displayed as scattered points with different colors/shapes, or different particle populations are distinguished by drawing respective boundaries or outlines. More specifically, the display unit visually and distinctively displays the fragmented red blood cells and at least one kind of red blood cells, reticulocytes, white blood cells, and platelets.

Figure 14A:
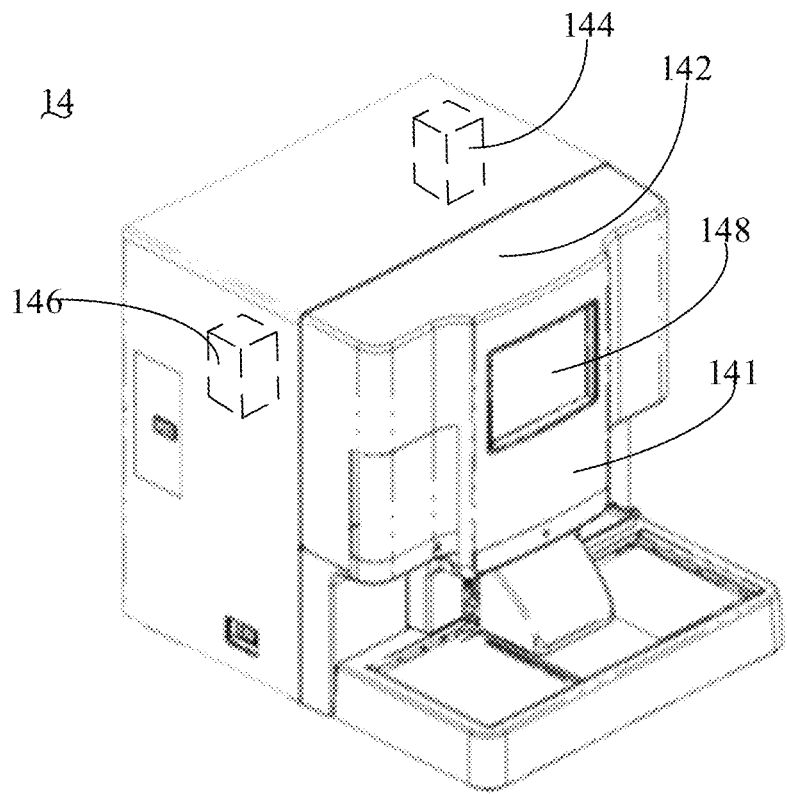
FIG. 14A and FIG. 14B respectively illustrate schematic structural diagrams of a blood analyzer according to an embodiment of the present application.
Figure 14B:
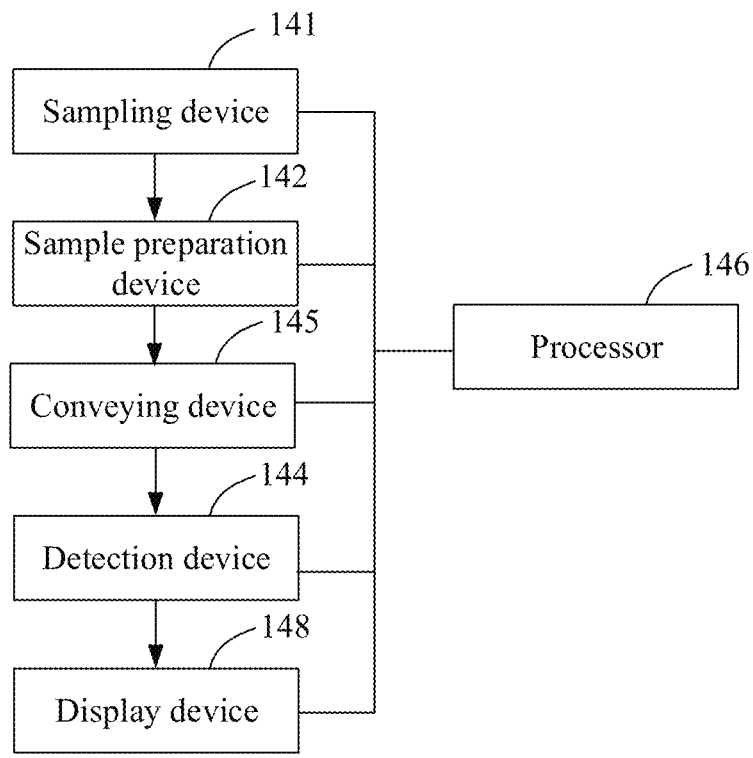

As a specific implementation for implementing the device for counting fragmented red blood cells, as shown in FIG. 14A and FIG. 14B, the present application also provides a blood cell analyzer 14. The blood cell analyzer 14 comprises a sample preparation device 142, a detection device 144, a conveying device 145, and a processor 146.

The sample preparation device 142 is configured to treat a blood sample with a reagent to prepare a sample liquid. In one embodiment, the blood cell analyzer 14 further comprises a sampling device 141 and a reagent injection device. The sampling device 141 is configured to collect a blood sample and convey the blood sample to the sample preparation device 142, and the reagent injection device is configured to inject the reagent into the sample preparation device 142. In this embodiment, the sampling device 141 is a sampling needle, and the sample preparation device 142 is configured to perform fluorescence staining treatment and spheroidization treatment on the blood sample, wherein cell membrane of each red blood cell can remain intact and internal structure of each white blood cell won't be damaged. It should be noted that the spheroidization treatment, which is intended to sphere red blood cells and reticulocytes with a surfactant to eliminate the influence of "directional noise" on measurement, is not necessary.

Thus, in the sample liquid formed by fluorescent staining the blood sample, the cell membrane of each red blood cell remains substantially intact.

The detection device 144 is configured to irradiate the sample liquid flowing through a detection area thereof with light, collect optical information generated by cell particles in the sample liquid in response to the light irradiation, and output electrical signals corresponding to the optical information of the cell particles. In this embodiment, the optical information of the cell particles collected by the detection device 144 includes side scattered light signals and fluorescence signals, so as to identify and distinguish a fragmented red blood cell population from the cell particles according to the foregoing optical information.

In one implementation, the detection device 144 comprises a light source, a flow chamber as the detection area, and a light collector and a photosensor disposed on an optical axis and/or a side edge of the optical axis. The sample liquid is surrounded with a sheath liquid and pass through the flow chamber, a light beam emitted from the light source irradiates the detection area, and the cell particles in the sample liquid pass one by one and emit fluorescence light and side scattered light in response to the irradiation by the light beam. The light collector collects and shapes the fluorescence signals and the side scattered light signals of the cell particles one by one. Then, the photosensor senses and converts the optical signals into corresponding electrical signals for output.

The conveying device is configured to convey the sample liquid in the sample preparation device 142 to the detection device 144. Specifically, the conveying device may comprise a conveying pipeline and a control valve, and the sample liquid is conveyed to the detection device 144 through the conveying pipeline and the control valve.

The processor 146 is configured to receive the optical information detected by the detection device 144, and distinguish and identify a fragmented red blood cell population from the cell particles according to the optical information.

In one embodiment, the processor 146 is specifically configured to count cell particles in the fragmented red blood cell population.

In one embodiment, the processor 146 is specifically configured to acquire a count value of a red blood cell population in the sample liquid and acquire a count ratio according to the count value of the fragmented red blood cell population and the count value of the red blood cell population.

For example, the processor 146 acquires the count value of the red blood cell population of the sample liquid by using other measurement methods such as an impedance method.

In one embodiment, the optical information includes forward scattered light, and the processor 146 is specifically configured to classify a red blood cell population according to the forward scattered light signals and the fluorescence signals of the cell particles, and acquire a count value of the fragmented red blood cell population and a count value of the red blood cell particle population according to the fragmented red blood cell population and the red blood cell population, and/or acquire a count ratio according to the fragmented red blood cell population and the red blood cell particle population.

In one embodiment, the optical information comprises forward scattered light, and the processor 146 is specifically configured to classify and/or count at least one kind of reticulocytes, white blood cells, and platelets according to the forward scattered light signals and the fluorescence signals. In one embodiment, the blood cell analyzer 14 further comprises a display device 148, and the display device 148 is connected to the processor 146 for displaying the fragmented red blood cell population. Specifically, the fragmented red blood cell population can be visually distinguished, for example, with a color or a shape, or by drawing a boundary or an outline, etc. More specifically, in the foregoing first two-dimensional scattergram or other two-dimensional or three-dimensional scattergrams, the red blood cells and the fragmented red blood cells can be visually and distinctively displayed on the first two-dimensional scattergram according to information characterizing the fragmented red blood cells, such as displayed as scattered points with different colors/shapes, or different particle populations are distinguished by drawing respective boundaries or outlines. Alternatively, in the foregoing second two-dimensional scattergram or other two-dimensional or three-dimensional scattergrams, red blood cells, white blood cells, platelets, and/or reticulocytes can be visually and distinctively displayed, for example, as scattered points with different colors/shapes, or different particle populations can be distinguished by drawing respective boundaries or outlines.

Figure 15:
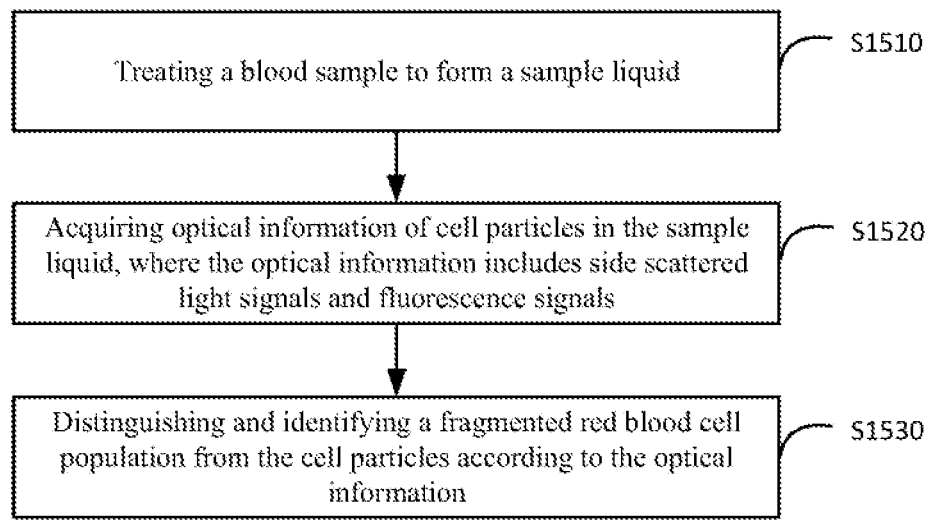
FIG. 15 illustrates a flowchart of a blood cell analysis method according to an embodiment of the present application.

As shown in FIG. 15, the present application further provides a blood cell analysis method, which comprises the following steps:

S1510: treating a blood sample to form a sample liquid.

In one implementation, a reagent is reacted with the blood sample in the sample preparation device 142 to acquire the sample liquid. The reagent comprises a fluorescent dye and a sphering component, and the fluorescent dye has cell permeability and can specifically stain the nucleic acid substance in cells. The sphering component is capable of sphering red blood cells. The reagent does not contain a hemolytic agent, and can keep the membrane of each red blood cell intact without damaging the internal structure of each white blood cell. Preferably, the reagent can contain an organic alcohol for increasing cell permeability and assisting the fluorescent dye to enter the cells.

S1520: acquiring optical information of cell particles in the sample liquid, where the optical information includes side scattered light signals and fluorescence signals.

In one implementation, the conveying device delivers the sample fluid in the sample preparation device 142 to the detection device 144 and makes the cells in the sample fluid pass through the detection area of the optical detection device 144 one by one. The detection device 144 irradiates the sample liquid with light, detects and collects forward scattered light signals, side scattered light signals, and fluorescence signals of the cell particles in the sample liquid one by one.

S1530: distinguishing and identifying a fragmented red blood cell population from the cell particles according to the optical information.

In one implementation, the processor 146 is specifically configured to distinguish and identify the fragmented red blood cell population from the cell particles according to the side scattered light signals and the fluorescence signals of the cell particles.

In one embodiment, step 1530 specifically comprises steps of:

acquiring a first two-dimensional scattergram according to the side scattered light signals and the fluorescence signals of the cell particles; and identifying cell particles falling within a preset region on the first two-dimensional scattergram as the fragmented red blood cell population.

In one embodiment, a cell population having an overall fluorescence intensity lower than that of a red blood cell population and an overall side scattered light intensity lower than that of the red blood cell population is identified as the fragmented red blood cell population. Specifically, on the first two-dimensional scattergram, cell particles located in a lower left region of the red blood cell population is identified as the fragmented red blood cell population. However, in some other implementations, it is not limited to the two-dimensional scattergram, which is not limited herein.

In one embodiment, after step S1530, the method further comprises a step of:

counting cell particles in the fragmented red blood cell population.

Specifically, a count value is acquired by counting cell particles in the fragmented red blood cell population.

In one embodiment, the blood cell analysis method further comprises a step of:

acquiring a count value of a red blood cell population in the sample liquid.

For example, the processor acquires the count value of the red blood cell population of the sample liquid by using other measurement methods such as an impedance method.

A count ratio is acquired according to the acquired count value of the fragmented red blood cell population and the count value of the red blood cell population.

Specifically, the processor 146 calculates the count ratio of the fragmented red blood cell population to the red blood cell population according to the count value of the fragmented red blood cell population and the count value of the red blood cell population.

Figure 16:
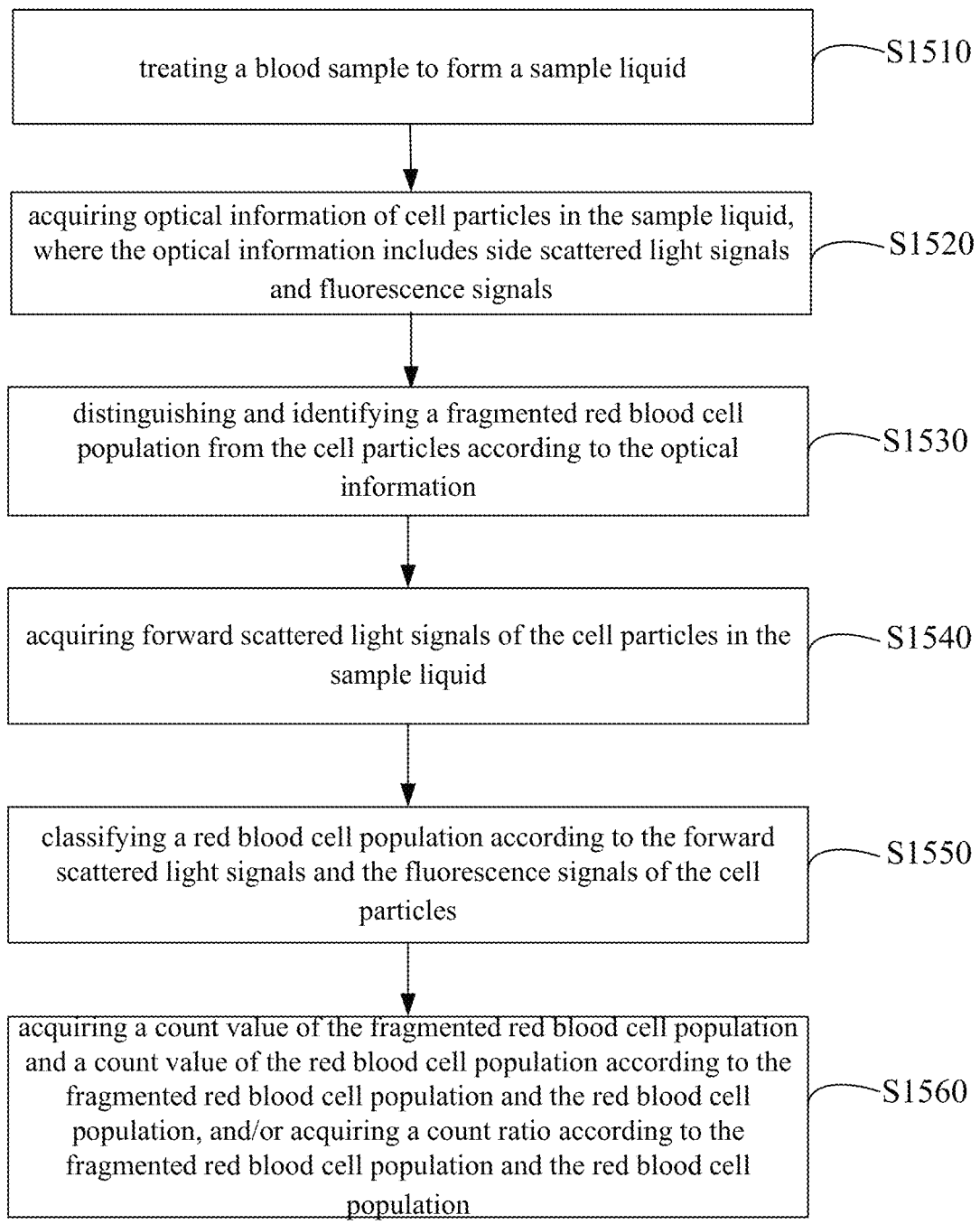
FIG. 16 illustrates a flowchart of a blood cell analysis method according to another embodiment of the present application.

As shown in FIG. 16, in another embodiment, the blood cell analysis method further comprises steps of:

S1540: acquiring forward scattered light signals of the cell particles in the sample liquid.

S1550: classifying a red blood cell population according to the forward scattered light signals and the fluorescence signals of the cell particles.

S1560: acquiring a count value of the fragmented red blood cell population and a count value of the red blood cell population according to the fragmented red blood cell population and the red blood cell population, and/or acquiring a count ratio according to the fragmented red blood cell population and the red blood cell population.

The corresponding count values can be acquired through counting the fragmented red blood cell population and the red blood cell population, and then the count ratio can be calculated. It is also possible to only acquire the count value by counting the red blood cell population identified according to the forward scattered light signals and the fluorescence signals of the cell particles. Certainly, the count ratio can also be directly acquired according to the fragmented red blood cell population and the red blood cell population, and it is not limited to firstly acquiring the count values of the two kinds of cell populations and then acquiring the count ratio.

In one embodiment, the blood cell analysis method further comprises steps of:

acquiring forward scattered light signals of the cell particles in the sample liquid; and classifying and/or counting at least one kind of reticulocytes, white blood cells, and platelets according to the forward scattered light signals and the fluorescence signals of the cell particles.

In one embodiment, step S1510 specifically comprises:

fluorescently staining the blood sample to form the sample liquid, where cell membranes of red blood cells in the sample liquid remain substantially intact.

In one embodiment, step S1510 further comprises a step of:

sphering the blood sample.

In one embodiment, the blood cell analysis method further comprises a step of:

displaying the fragmented red blood cell population.

Specifically, the fragmented red blood cell population is displayed by distinctively displaying the fragmented red blood cells and other blood cells in a visual way, for example, with a color or a shape, or by drawing a boundary or an outline, etc. More specifically, in the foregoing first two-dimensional scattergram or other two-dimensional or three-dimensional scattergrams, the red blood cells and the fragmented red blood cells can be visually and distinctively displayed on the first two-dimensional scattergram according to information characterizing the fragmented red blood cells, such as displayed as scattered points with different colors/shapes, or different particle populations are distinguished by drawing respective boundaries or outlines.

In one embodiment, the blood cell analysis method further comprises a step of:

acquiring a second two-dimensional scattergram according to the forward scattered light signals and the fluorescence signals of the cell particles; and visually and distinctively displaying the fragmented red blood cells and at least one kind of red blood cells, reticulocytes, white blood cells, and platelets on the second scattergram.

It should be understood that in an actual detection application, the detection device 144 of the blood analyzer can collect forward scattered light signals, side scattered light signals, and fluorescence signals of the cell particles in the sample liquid. The processor 146 can identify one, two or more kinds of cell particles such as a red blood cell population, a fragmented red blood cell population, a platelet population, a white blood cell population, and a reticulocyte population according to the aforementioned optical information of the cell particles. The display device can display the acquired scattergram and distinctively display the fragmented red blood cells and at least one kind of the red blood cells, the reticulocytes, the white blood cells, and the platelets on the scattergram in a visual away. Certainly, the display device is not limited to visually display a scattergram, but may also display other two-dimensional or three-dimensional plots. That is, the blood analyzer can simultaneously collect various kinds of optical information of cell particles and respectively detect and identify different cell particles. It is different from a processor 146 of a conventional blood cell analyzer that a fragmented red blood cell population can be detected and identified according to side scattered light signals and fluorescence signals, thereby acquiring a count value and/or a count ratio of the fragmented red blood cell population and a red blood cell population.

It will be understood that, a person skilled in the art can appreciate that the modules and method steps described in combination with the examples disclosed herein can be implemented using electronic hardware, computer software, or any combination thereof. Whether such functionality is implemented as hardware or software depends upon the particular application of the technical solution and design constraints. A person skilled in the art may implement the described functionality in varying ways for each particular application, but such implementations should not be interpreted as causing a departure from the scope of the present application.

For example, the step of acquiring side scattered light signals and fluorescence signals of cell particles in a sample liquid may be implemented with software, and can also be implemented with hardware. For example, an optical detection device irradiates the cell particles in the sample liquid with light, and then detects and collects the side-scattered light signals and the fluorescence signals of the cell particles.

In the embodiments of the present application, the disclosed device and method may be implemented in other manners. For example, the embodiments of the foregoing device are merely illustrative. For example, the division of units is only a division of logical functions, and in actual implementations, there may be other division methods in actual implementations. For example, multiple units may be combined or may be integrated in one system.

When being implemented as a software function unit and sold or used as a stand-alone product, the functionality of the unit may be stored in a computer-readable storage medium. Based on such understanding, the technical solution of the present application substantially, or the part thereof that contributes to the prior art, may be embodied in a software product. The computer software product is stored in a storage medium and includes instructions for causing a computer device to execute all or part of the steps of the methods described in any embodiments of the present application.

The foregoing storage medium may be any medium that can store program code, such as a USB flash disk, a mobile hard disk, a read only memory, or a random access memory.

The technical features of the above-described embodiments may be combined in any combination. For the sake of brevity of description, the various technologies in the above embodiments are not described in all possible combinations. However, as long as no contradiction occurs in a combination of these technical features, the combination should be considered to fall within the scope of the present specification.

The above-described embodiments are merely illustrative of several embodiments of the present application, and the description thereof is specific and detailed, but it is not to be construed as limiting the scope of the application. It should be noted that for a person of ordinary skill in the art, several variations and improvements can be made without departing from the spirit of the present application, which shall fall within the scope of the application. Accordingly, the protection scope of the present patent shall be subject to the appended claims.

The invention claimed is:

1. A blood cell analyzer, comprising:
   a sampling device;
   a sample preparation device;
   a conveying device;
   a detection device; and
   a processor;
   wherein the processor is programmed with and executes processor-executable instructions to:
   control the sampling device to collect a blood sample;
   control the sample preparation device to treat the blood sample conveyed by the sampling device with a reagent to prepare a sample liquid;
   control the conveying device to convey the sample liquid in the sample preparation device to the detection device and to pass cell particles in the sample liquid through a detection area of the detection device one by one;
   control the detection device to irradiate the sample liquid with light and collect side scattered light signals and fluorescence signals in optical information generated by the cell particles in the sample liquid in response to the light irradiation; and
   receive the side scattered light signals and fluorescence signals collected by the detection device, construct a two-dimensional scattergram according to the side scattered light signals and the fluorescence signals of the cell particles, and distinguish and identify cell particles falling within a preset region on the two-dimensional scattergram as a fragmented red blood cell population.

2. The blood cell analyzer according to claim 1, wherein the processor is further programmed with and executes processor-executable instructions to count cell particles in the fragmented red blood cell population.

3. The blood cell analyzer according to claim 1, wherein the processor is further programmed with and executes processor-executable instructions to control the detection device to collect forward scattered light signals in the optical information, classify a red blood cell population according to the forward scattered light signals and the fluorescence signals of the cell particles, and acquire a count value of the fragmented red blood cell population and a count value of the red blood cell population according to the fragmented red blood cell population and the red blood cell population, and optionally acquire a count ratio according to the fragmented red blood cell population and the red blood cell population.

4. The blood cell analyzer according to claim 1, wherein the processor is further programmed with and executes processor-executable instructions to control the sample preparation device to treat the sample liquid, such that the cell particles in the sample liquid are fluorescently stained, and cell membranes of red blood cells remain substantially intact.

5. The blood cell analyzer according to claim 1, wherein the processor is further programmed with and executes processor-executable instructions to control the detection device to collect forward scattered light signals in the optical information, and classify and optionally count at least one kind of reticulocytes, platelets, and white blood cells according to the forward scattered light signals and the fluorescence signals of the cell particles.

6. The blood cell analyzer according to claim 1, wherein the blood cell analyzer further comprises a display device, which display device is connected to the processor and controlled by the processor to distinctively display the fragmented red blood cell population in a visual way.

7. The blood cell analyzer according to claim 1, wherein the processor is further programmed with and executes processor-executable instructions to compare two-dimensional scattergrams of normal human blood samples and blood samples containing fragmented red blood cells, conduct statistical analysis to acquire a specific region on the two-dimensional scattergram of the blood samples containing fragmented red blood cells, and determine the specific region as the preset region.

8. The blood cell analyzer according to claim 1, wherein the processor is further programmed with and executes processor-executable instructions to compare two-dimensional scattergrams of normal human blood samples and blood samples containing fragmented red blood cells, conduct statistical analysis to acquire a function of a relative position between a fragmented red blood cell population region and a red blood cell population region, and determine, by using the function of the relative position, the preset region according to an identified red blood cell population region on the constructed two-dimensional scattergram.

9. The blood cell analyzer according to claim 1, wherein the processor is further programmed with and executes processor-executable instructions to determine a specific region located at a lower left of a red blood cell population on the constructed two-dimensional scattergram as the preset region.

* * * * *